US010870649B2

(12) United States Patent
Lattuada et al.

(10) Patent No.: US 10,870,649 B2
(45) Date of Patent: Dec. 22, 2020

(54) SYNTHESIS OF NIR FLUORESCENT PROBE

(71) Applicant: BRACCO IMAGING SPA, Milan (IT)

(72) Inventors: Luciano Lattuada, Cassina de' Pecchi (IT); Federica Buonsanti, Turin (IT); Federico Crivellin, Caselle Torinese (IT); Fulvio Ferretti, Feletto Canavese (IT); Federico Maisano, Lodi (IT); Laura Orio, Turin (IT); Lorena Pizzuto, San Francesco al Campo (IT)

(73) Assignee: BRACCO IMAGING SPA, Milan (IT)

( * ) Notice: Subject to any disclaimer, the term of this patent is extended or adjusted under 35 U.S.C. 154(b) by 0 days.

(21) Appl. No.: 16/604,430

(22) PCT Filed: Apr. 10, 2018

(86) PCT No.: PCT/EP2018/059083
§ 371 (c)(1),
(2) Date: Oct. 10, 2019

(87) PCT Pub. No.: WO2018/189136
PCT Pub. Date: Oct. 18, 2018

(65) Prior Publication Data
US 2020/0055855 A1 Feb. 20, 2020

(30) Foreign Application Priority Data
Apr. 13, 2017 (EP) .................... 17166432

(51) Int. Cl.
C07D 471/18 (2006.01)
A61K 49/00 (2006.01)
C09B 23/08 (2006.01)

(52) U.S. Cl.
CPC ........ C07D 471/18 (2013.01); A61K 49/0032 (2013.01); A61K 49/0056 (2013.01); C09B 23/083 (2013.01)

(58) Field of Classification Search
CPC .................................................. C07D 471/18
See application file for complete search history.

(56) References Cited

U.S. PATENT DOCUMENTS

2014/0288300 A1 9/2014 Kim et al.

FOREIGN PATENT DOCUMENTS

| CN | 102010614 A | 4/2011 |
| EP | 1801086 A1 | 6/2007 |
| WO | 2016097317 A1 | 6/2016 |

OTHER PUBLICATIONS

Bat, M. et al. "Recent Advances in Receptor-Targeted Fluorescent Probes for in Vivo Cancer Imaging," Current Medicinal Chemistry, 19(28):4742-4758 (2012).

Chevalier, A. et al. "Azo-Sulforhodamine Dyes: A novel class of broad Spectrum Dark Quenches," Organic Letters, 16(15):3946-3949 and Supporting Information (2014).
International Search Report and Written Opinion for PCT/EP2018/059083, dated Jun. 7, 2018.
Lanzardo, S. et al., "A New Optical imaging probe targeting αVβ3 integrin in glioblastoma xenografts," Contrast Media & Mol. Imaging, 6:449-458 (2011).
Manzoni, L. et al. "Cyclic RGD-Containing Functionalized Azabicycloalkane Peptides as Potent Integrin Antagonists for Tumor Targeting," ChemMedChem, 4:615-632 and Supporting Information (2009).

(Continued)

Primary Examiner — Noble E Jarrell
(74) Attorney, Agent, or Firm — Vivicar Law, PLLC

(57) ABSTRACT

The application relates to a process for the synthesis of a Near Infra-Red (NIR) fluorescent probe which is a cRGD-Cy5.5 conjugate of formula (I) known as DA364 comprising an aza-bicycloalkane based cyclic peptide labelled with a Cy5.5 dye moiety and used in the guided surgery of tumors and pathologic regions.

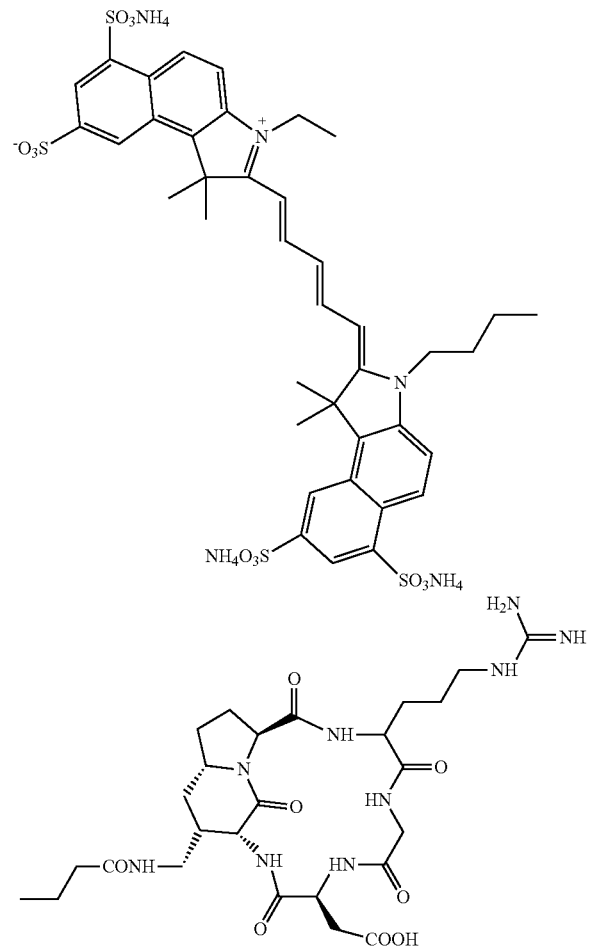

15 Claims, No Drawings

(56) References Cited

OTHER PUBLICATIONS

Mujumdar, S., et al. "Cyanine-Labeling Reagents: Sulfobenzindocyanine Succinimidyl Esters," Bioconjugate Chem., 7:356-362 (1996).

SYNTHESIS OF NIR FLUORESCENT PROBE

CROSS-REFERENCE TO RELATED APPLICATIONS

This application is the national stage application of corresponding international application number PCT/EP2018/059083, filed Apr. 10, 2018, which claims priority to and the benefit of European application no. 17166432.9, filed Apr. 13, 2017, all of which are hereby incorporated by reference in their entirety.

FIELD OF THE INVENTION

The present invention relates to the field of optical imaging. More in particular, it relates to an improved process of synthesis of a Near Infra-Red (NIR) fluorescent probe (known as "DA364") comprising an aza-bicycloalkane based cyclic peptide labelled with a Cy5.5 dye moiety and used in the guided surgery of tumors and pathologic regions.

BACKGROUND

DA364 (see formula I below) is a NIR fluorescent agent effectively used in the intraoperative imaging to provide a real-time detection and demarcation of tumor margins during the NIR-fluorescence imaging guided curative surgery of tumors.

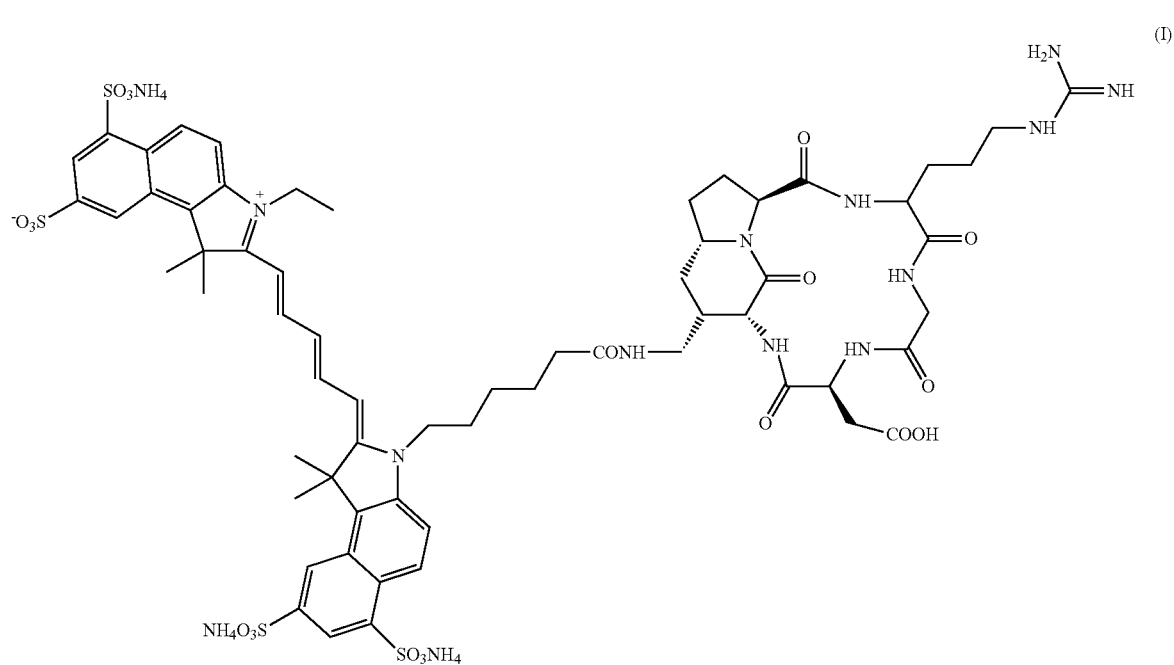

The synthesis of DA364 (see Lanzardo et al., *Contrast Media Mol. Imaging* 2011, 6, 449-458) involves the reaction of succinimidyl ester (VI) (Cy5.5-NHS) with peptidomimetic (VII) (amino-cyclic cRGD), obtained by catalytic reduction of the corresponding azide compound (II), according to the following reaction scheme 1:

Scheme 1
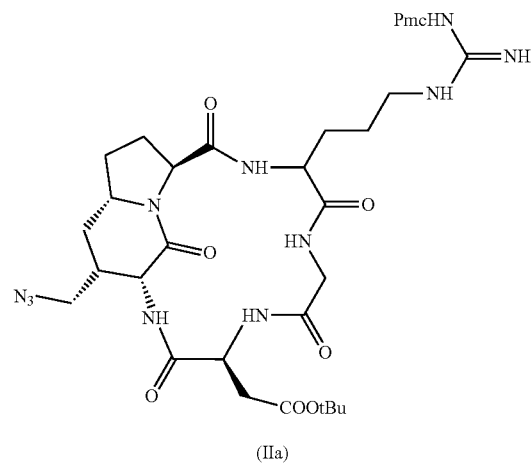
(IIa)
1) H₂, Pd/C
2) TFA
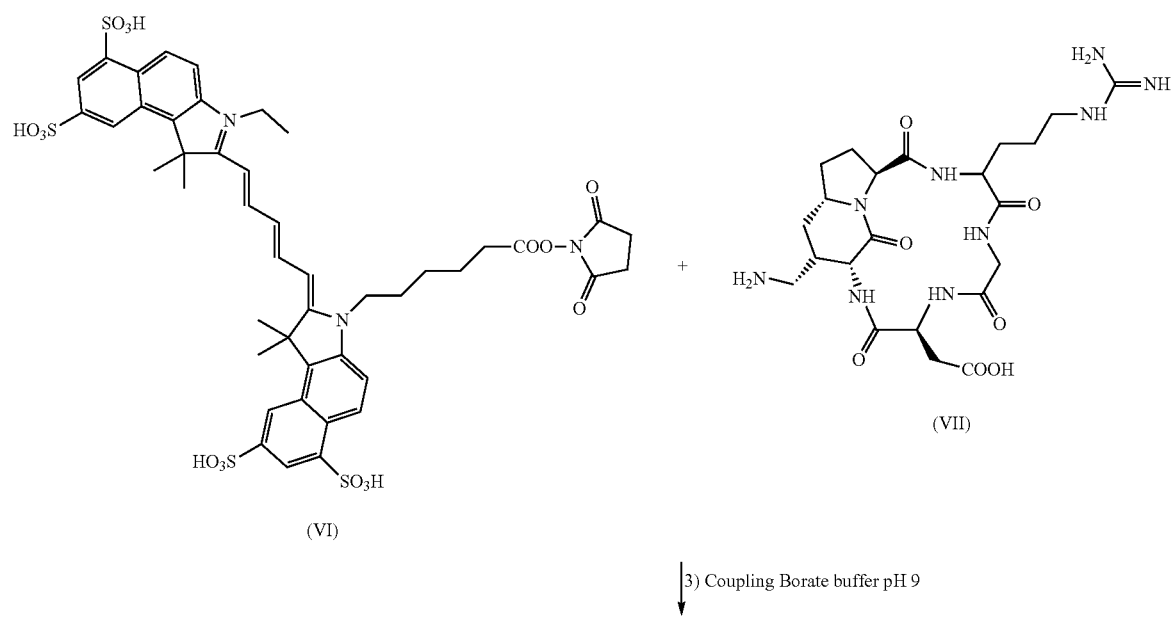
(VI)    (VII)
3) Coupling Borate buffer pH 9

-continued

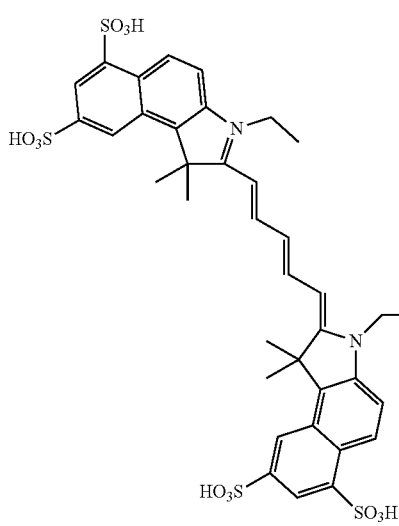
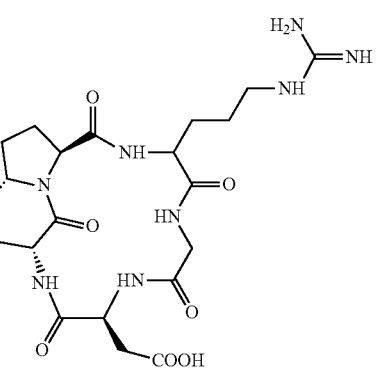

DA364
(I)

This process has however some drawbacks in terms of scaling up, time and costs. In particular, the synthesis of Cy5.5-NHS (VI) is lengthy and the final cyanine NHS ester is difficult to purify resulting in an overall low yield. Moreover, being an activated ester, it is unstable and it cannot be successfully stored as dry solid, thus requiring to be synthesized immediately before use. Additionally, the synthesis of the amino-cyclic cRGD (VII) from compound (IIa) requires several steps, not only for hydrogenation but also for deprotection and purification by preparative HPLC of the deprotected compound (VII) from any side products. The crude DA364 must be purified by preparative HPLC as well, to avoid the presence of side products.

The applicant has now developed an improved synthesis of DA364 starting from Cy5.5-COOH derivative instead of the Cy5.5-NHS and holding the protecting groups on the cRGD amino acids up to the coupling reaction, which allows overcoming some drawbacks of currently known preparation methods.

In general, the direct amide coupling between an nonactivated carboxylic acid and an amine in the presence of a coupling reagent has been already disclosed in the prior art as alternative way for the preparation of imaging probes: for instance, it is cited in Bai M. et al, Curr. Med. Chem. 2012, 19(28), 4742-4758.

Some examples of conjugates obtained with this approach are also disclosed in US 2014/288300 A1, in the name of Korean Institute of Science and Technology, and in Chevalier et al., Org. Lett. 2014, 16, 3946-3949, reporting the preparation of conjugates with fluorophores-COOH and amines in the presence of a coupling agent such as HATU or PyBOP.

However, no hints were found in the background art providing an expectation of success in applying this approach to the whole synthesis of DA364, with aim of solving the above cited drawbacks and obtaining an improvement in the yield as well as time and costs of the process.

Definitions

In the present description, and unless otherwise provided, the term "coupling reagent" refers to a reagent used in the formation of an amide bond between a carboxyl moiety and an amino moiety. The reaction consists of two consecutive steps: activation of the carboxyl moiety and then acylation of the amino group. Coupling reagents typically include at least phosphonium, aminium, imonium, imide functionalities which are able to react with the respective carboxyl group to give an intermediate attacked by the amino moieties. Examples of coupling agents are reported below.

The expression "anhydrous polar aprotic solvent" includes dry solvents with a relatively large dielectric constant (e.g. >20) that have dipoles due to polar bonds but don't have H atoms that can be donated into a H-bond. Examples of anhydrous polar aprotic solvent include, for instance, N,N-dimethylformamide, N,N-dimethylacetamide, dimethyl sulfoxide, N-methylpyrrolidinone, acetonitrile.

The expression "acid scavenger cocktail" includes within its meaning a cleavage acid reagents mixture suitable for removing some protecting groups, particularly Mtr (2,3,6-trimethyl-4-methoxybenzene-sulfonyl), Pmc (2,2,5,7,8-pentamethyl-6-chromane-sulfonyl), OtBu (tert-butyl ester), Trt (triphenylmethyl), Pbf (2,2,4,6,7-pentamethyl-2,3-dihydro-1-benzofuran-5-sulfonyl). Examples of acid scavenger cocktail are reported below.

SUMMARY OF THE INVENTION

The invention relates to a process for the preparation of a cRGD-Cy5.5 conjugate of formula (I)

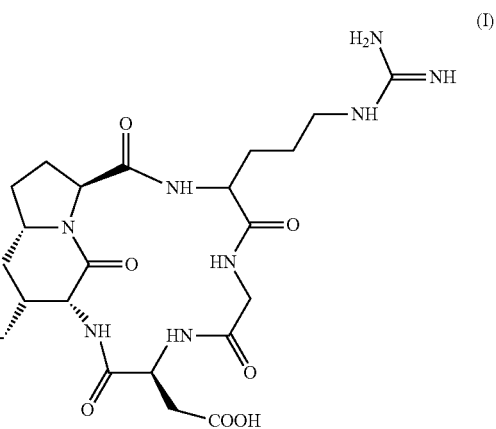
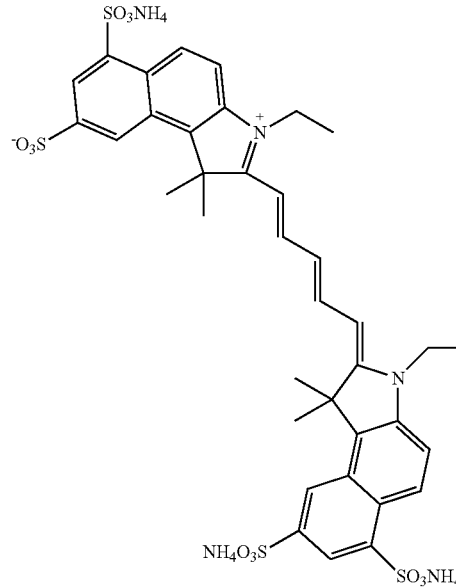
which comprises the steps of:
a) hydrogenating a compound of formula (II)
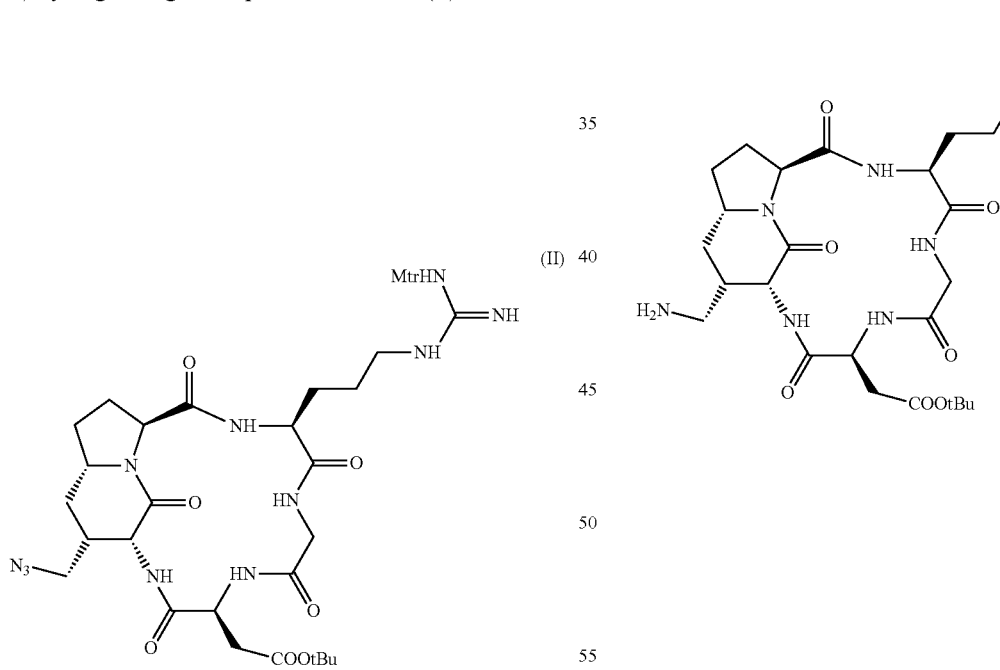
wherein Mtr is a 2,3,6-trimethyl-4-methoxybenzenesulfonyl group, to provide its amino-derivative of formula (III)
wherein Mtr is as defined above;
b) reacting, in the presence of a base and a coupling reagent, the compound of formula (III) with a compound of formula (IV)

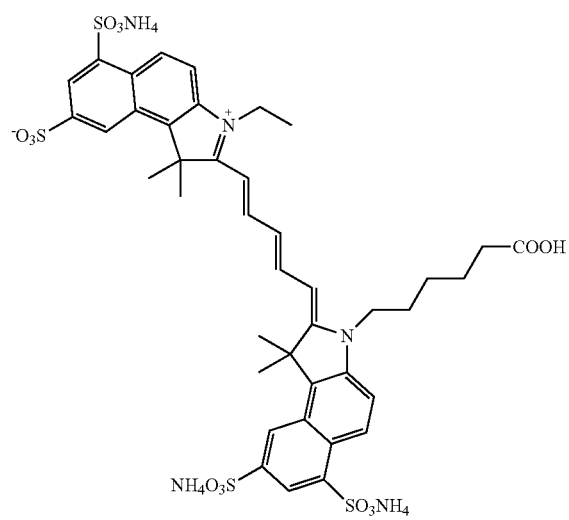

(IV)

to provide a compound of formula (V)

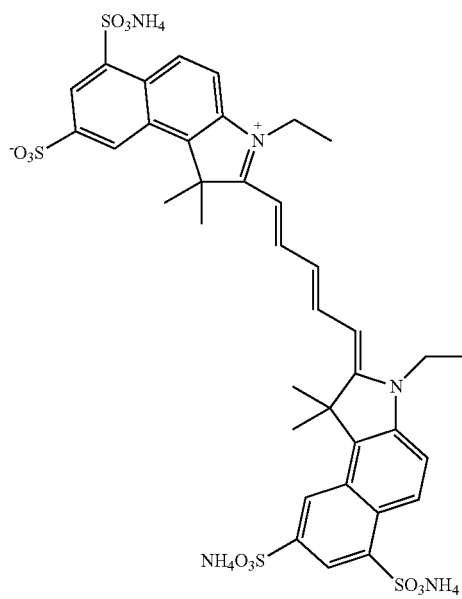

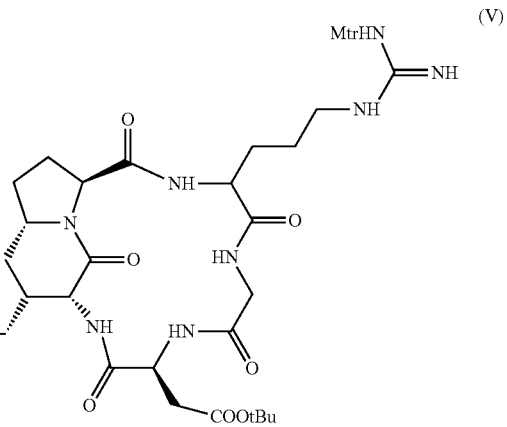

(V)

wherein Mtr is as defined above;
c) deprotecting the compound of formula (V) to obtain the compound of formula (I).

The new synthetic approach, object of the present invention, provides for a most effective process for the preparation of DA364 with final yields increased of at least 12% and affords several improvements particularly advantageous in industrial scale production.

In fact, the selection, instead of Cy5.5-NHS, of the less reactive but more stable Cy5.5-COOH derivative allows the storage of the starting material without degradation problems.

Moreover, the strategy of removing the amino acids protecting groups only after the coupling of the cyanine with the cRGD peptide has been unexpectedly proved to be beneficial for several reasons: for instance it avoids the formation of undesired by-products; it avoids the purification step of the azide compound (II), which is used as such without purification; it facilitates the chromatographic separation and purification of the conjugate from the unreacted cyanine, which can also be easily recovered and recycled. Lastly, the coupling can be carried out in anhydrous polar aprotic solvent instead of borate buffer, again offering the opportunity to store the intermediate without degradations.

Several of the above achievements have been surprisingly obtained, even in the absence of prior teachings. In particular, no evidences were found in the prior art about the stability of the cRGD-Cy5.5 conjugate to the strongly acid conditions applied in the final deprotection step, carried out in the presence of acid scavenger cocktails.

Nevertheless, the present invention provides for a process wherein the DA364 is obtained in good yield and without degradation, even in the presence of strong acidic conditions.

Moreover, the purification steps in the present process are dramatically simplified, thanks to the removal of inconvenient HPLC preparative steps, for instance before the coupling, or the addition of easier and quicker purifications by flash chromatography. In fact, it has been surprisingly found that using for instance an anion exchange chromatography performed with an agarose matrix resin it is possible to separate the final conjugate compound from the non coupled cyanine, thus improving the subsequent HPLC purification step,

DETAILED DESCRIPTION OF THE INVENTION

The present invention discloses a process for the preparation of a cRGD-Cy5.5 conjugate of formula (I), known in the art as DA364, as shown in the following scheme 2:

Scheme 2
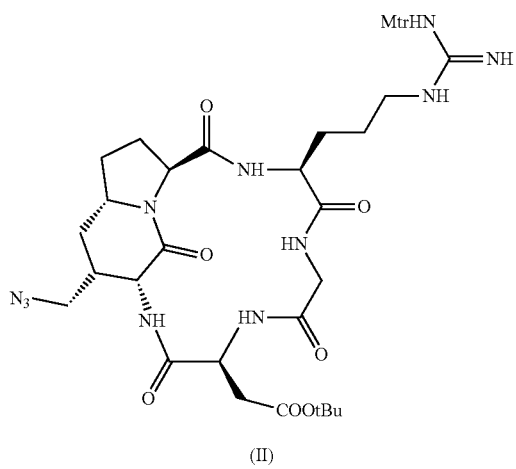
(II)
a) Hydrogenation ↓
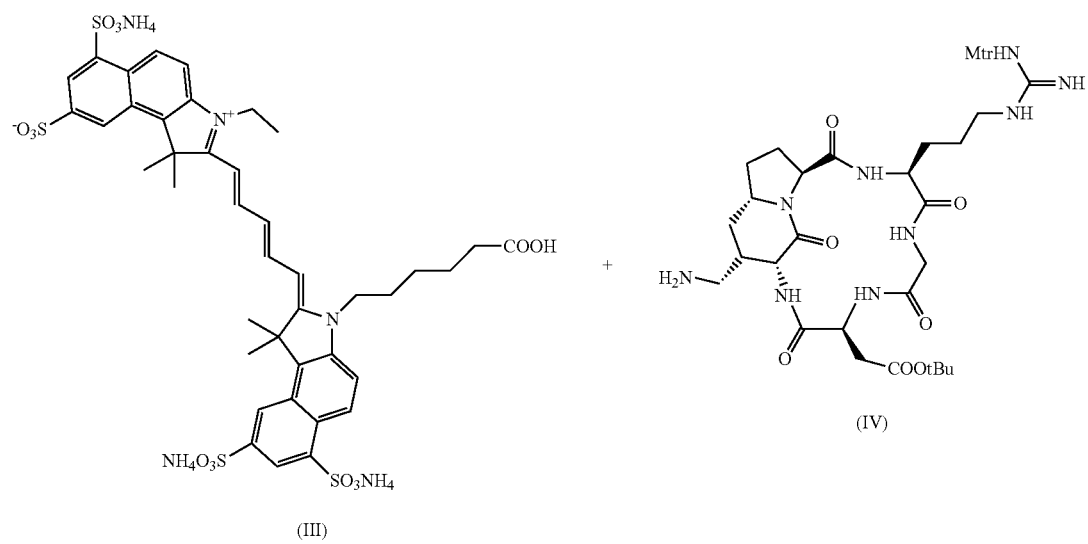
b) Coupling ↓

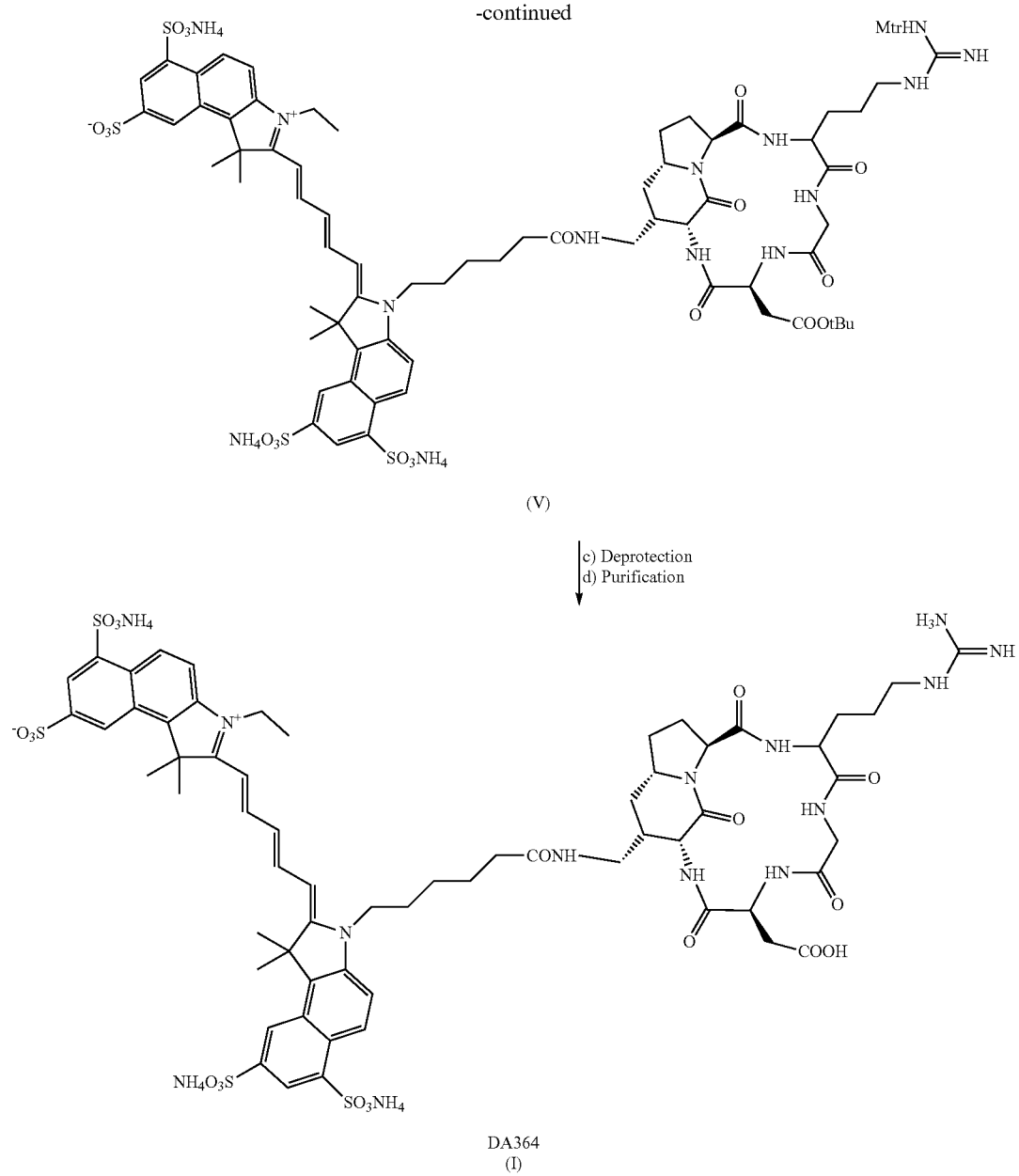

(V)

c) Deprotection
d) Purification

DA364
(I)

The first step of the present process involves the hydrogenation of the intermediate compound (II) to obtain the protected cRGD compound (III). Differently from the process disclosed by Lanzardo et al., the protective groups on aspartic acid and arginine of compound (III) are not removed in order to avoid the formation of by-products, making purification unnecessary. The azide compound (II) can be synthesized for example according to the procedure described in Manzoni et al., Chem. Med. Chem 2009, 4, 615-632.

According to step a), compound (II) is thus dissolved in a suitable solvent, preferably an alcohol, such as, for instance, methanol, ethanol, isopropanol, t-butanol, more preferably methanol, or a mixture of them. In general, the azide may be dissolved in a concentration of from 3 mM to 7 mM, preferably from 5 to 5.5 mM, more preferably 5 mM.

The reduction of the azido group of compound (II) to the amino group of compound (III) can be performed by flowing (e.g. 0.2-0.8 ml/min, preferably 0.5 ml/min) the solution through a metal catalyst (e.g. in the form of a cartridge) under hydrogen atmosphere at room temperature. The metal catalyst is preferably palladium or platinum, more preferably palladium. In a preferred embodiment the metal catalyst is admixed with a suitable supporting material e.g. carbon powder, in a preferred amount of from 5 to 10% (by weight) of metal catalyst.

The reaction can be carried out at a temperature of from 18° C. and 40° C., preferably between 20° C. and 30° C. and even more at room temperature (i.e. around 22° C.).

The reaction can be carried out in a flow reactor system (continuous mode) or in batch conditions.

The second step of the process involves the coupling of the carboxylic acid of Cy5.5 (intermediate compound (IV)) to the amino group of compound (III) to obtain the crude DA364 compound.

According to step b), the coupling is effected in the presence of an anhydrous polar aprotic solvent. The solvent is preferably selected from the group consisting of dry N,N-dimethylformamide, N,N-dimethylacetamide, dimethyl sulfoxide, N-methylpyrrolidinone, acetonitrile and the like, preferably dry N,N-dimethylformamide.

Cy5.5-COOH compound (IV) may be dissolved in the solvent in a concentration of from 5 to 10 mM, preferably from 7 to 9 mM, more preferably 8.6 mM. Cy5.5-COOH compound (IV) is a commercially available compound (Lumiprobe, cat.#17390). Alternatively it can be synthetized starting from 6-amino-1,3-naphthalenedisulfonic acid disodium salt according to the procedures described in Mujumdar et al., *Bioconjugate Chem.* 1996, 7, 356-362 and in CN102010614A. It can be coarsely purified by flash chromatography saving a lot of time compared to the prior art procedure which required the preparative HPLC purification. As said above, Cy5.5-COOH compound (IV) is less reactive than the corresponding ester (VI) (used in the known preparation method) and it can be stored.

Due to the relatively low reactivity of intermediate compound (IV), it is necessary to use a coupling reagent for performing the reaction between compound (IV) and compound (III). The coupling reagent can be selected from the group consisting of N,N,N',N'-tetramethyl-O-(benzotriazol-1-yl)uronium tetrafluoroborate (TBTU), 4-(4,6-dimethoxy-1,3,5-triazin-2-yl)-4-methylmorpholinium chloride (DMTMM), (benzotriazol-1-yloxy)tris(dimethylamino)phosphonium hexafluorophosphate (BOP), (benzotriazol-1-yloxy)tripyrrolidinophosphonium hexafluorophosphate (PyBOP) N,N,N',N'-tetramethyl-O-(7-azabenzotriazol-1-yl)uronium hexafluorophosphate (HATU), N,N,N',N'-tetramethyl-O-(1H-benzotriazol-1-yl)uronium hexafluorophosphate (HBTU), propylphosphonic anhydride (T3P®), preferably TBTU. The ratio between the intermediate compound (IV) and the coupling reagent can be of from 1:1 to 1:5 (mol/mol), preferably from 1:1.5 to 1:3 and more preferably about 1:2.

The activation is also promoted by the addition of a base to the reaction mixture. Further to deprotonating the carboxylic acid of Cy5.5-COOH compound (IV), the base advantageously acts as a pH buffer neutralizing the residual acidity. The base can be chosen among N,N-diisopropylethylamine (DIPEA), triethylamine (TEA), tributylamine, N-methylpiperidine or N-methylmorpholine, preferably N-methylmorpholine. The ratio between the intermediate compound (IV) and the base can be of from 1:3 to 1:6 (mol/mol), preferably from 1:3.5 to 1:5 and more preferably about 1:4.

The coupling is preferably performed under stirring, in the dark and under $N_2$ atmosphere for 1-8 h, preferably 3 h. It is preferably carried out at a temperature of from 20° C. to 25° C., more preferably at room temperature.

The proposed synthesis of DA364 is very specific, as the protective groups on cRGD compound (III) avoid the formation of side products due to the reaction of the arginine of cRGD compound (III) with the carboxylic group of Cy5.5 compound (IV).

The third step involves the deprotection of the t-butyl ester and the 2,3,6-trimethyl-4-methoxybenzenesulfonyl (Mtr) group still on the peptidomimetic moiety, obtaining crude DA364.

According to step c), the functional group deprotection reaction may be carried out in accordance with known techniques with efficient acid scavenger cocktails such us trifluoroacetic acid/phenol/thioanisole/1,2-ethanedithiol/water, trifluoroacetic acid/thioanisole/1,2-ethanedithiol/anisole or trifluoroacetic acid/phenol/water/triisopropylsilane, preferably trifluoroacetic acid/thioanisole/1,2-ethanedithiol/anisole, wherein the ratio between trifluoroacetic acid, thioanisole, 1,2-ethanedithiol and anisole is of from 70:15:10:5 to 90:5:3:2, preferably 90:5:3:2.

The deprotection can be performed under stirring, at room temperature and in the dark for 1-8 h, preferably 2 h.

According to step d), the purification of crude DA364 is performed through a combination of conventional techniques. Preferably, pure DA364 product can be obtained after a two-step purification process, comprising an anion exchange chromatography step followed by preparative HPLC.

The anion exchange chromatography step can be performed in a buffer of 20 mM Tris-HCl at a pH of from 7 to 8, preferably 7.5, by gradient or isocratic elution with 0-100% 1 M NaCl, or, preferably, by a three step isocratic elution, respectively with 10-30% of 1 M NaCl, 70-100% of 1 M NaCl and 1 M NaCl, 30% isopropanol. The anion exchange chromatography resin is a strong or a weak anion exchanger, preferably a quaternary ammine group bound to a solid matrix, preferably agarose beads.

Preparative HPLC can be performed with a gradient from 0 to 100%, preferably from 2 to 95%, of acetonitrile in ammonium acetate buffer 0.1%. Alternatively, it can be performed by isocratic elution with 20-30%, preferably 20%, of acetonitrile and 70-80%, preferably 80%, of 8 g/l ammonium acetate. The HPLC column is a silica RP column, preferably Phenyl bonded phase.

With this strategy, purification steps are reduced saving a lot of time and costs.

The following examples further illustrate the invention.

Example 1: Synthesis of DA364

Materials and Equipment

All commercially available reagents employed in the synthesis of DA364 were used without further purification. The intermediate compound (II) was synthesized according to the procedures described in Manzoni et al., *Chem. Med. Chem.* 2009, 4, 615-632; except that arginine was protected with 2,3,6-trimethyl-4-methoxybenzenesulfonyl (Mtr) protective group instead than 2,2,5,7,8-pentamethylchroman-6-sulfonyl (Pmc) protective group. Compound (IV) was synthesized according to the procedures described in Mujumdar et al., *Bioconjugate Chem.* 1996, 7, 356-362 and in CN102010614A and coarsely purified on a C18 cartridge using a Combiflash automated purification system with a 10% to 100% gradient of acetonitrile in 0.1% formic acid aqueous solution.

The hydrogenation step was performed on a flow reactor with a 10% Pd/C cartridge.

The reactions were followed using MS-HPLC with an absorption detector with wavelengths set at 220 nm, 254 nm, 677 nm.

The final compound purification was performed with FPLC system followed by preparative RP-HPLC.

UV-Vis/NIR absorption spectra were recorded on Analytic Jena, Specord 200 Plus spectrophotometer.

Synthesis of DA364

The synthesis of DA364 is carried out according to scheme 2.

Hydrogenation. Azide compound (II) (0.39 mmol) was dissolved in methanol (80 ml) and the solution was passed through the 10% palladium cartridge under hydrogen atmosphere. After two cycles the resulting product was collected and the solution was concentrated in vacuo. Compound (III) was used without further purification.

Coupling. The crude intermediate compound (III) was added to a solution of compound (IV) (0.43 mmol), N-methylmorpholine (1.73 mmol) and TBTU (0.86 mmol) in dry dimethylformamide (50 ml) to give a dark blue solution. The reaction was allowed to stir in the dark under $N_2$ atmosphere for 3 h; upon completion of the reaction, the solvent was evaporated and the crude product was treated as described below to remove the protecting groups without any further purification.

Deprotection. A TFA/scavenger cocktail (trifluoroacetic acid, thioanisole, ethanedithiol, anisole, 90:5:3:2, 20 ml total), freshly prepared, was added to the crude obtained in the previous step and the mixture was allowed to stir at room temperature for 2 h in the dark. The reaction mixture was then evaporated and the blue oil was dissolved in water (100 ml) and washed with diethyl ether or isopropyl ether (2×30 ml). Pure DA364 product was obtained after a double-step purification process.

Purification. The process comprises an anion exchange chromatography step, performed with commercially available agarose matrix resin (70 ml) wherein a linear NaCl gradient in a buffer comprising 20 mM Tris-HCl at a pH of about 7 was used, and a reverse phase high performance liquid chromatography step performed with YMC-Triart Phenyl preparative column (250×50 mm) wherein a linear gradient from 0 to 95% acetonitrile in ammonium acetate buffer was used.

After purification, pure DA364 compound was obtained as a blue freeze-dried powder in 36% yield (0.14 mmol) with respect to azide compound (II).

Comparative Example 2: Comparative Synthesis of DA364

DA364 was obtained according to the procedure described by Lanzardo et al., *Contrast Media Mol. Imaging* 2011, 6, 449-458 by following the synthetic procedure reported in scheme 1.

Materials and Equipment

All commercially available reagents employed in the synthesis were used without further purification. The intermediate compound (II) was synthesized according to the procedures described in Manzoni et al., Chem. Med. Chem. 2009, 4, 615-632; the intermediate (VII) was purified by RP-HPLC and used in the following step as freeze-dried powder.

The hydrogenation step was performed by The H-Cube Pro™ flow reactor with a 10% Pd/C cartridge.

The coupling reaction was followed using MS-HPLC with an absorption detector with wavelengths set at 220 nm, 254 nm, 677 nm.

The final compound purification was performed with preparative RP-HPLC.

Synthesis of DA364

Azide compound (II) (1.43 mmol) was dissolved in MeOH (150 ml) and the solution was passed through the 10% palladium cartridge under hydrogen atmosphere. After two cycles the resulting product was collected. The collected solution was concentrated in vacuo and TFA/scavenger cocktail (trifluoroacetic acid, thioanisole, ethanedithiol, anisole, 90:5:3:2, 20 ml total), freshly prepared, was added. The mixture was stirred at room temperature for 2 h in the dark. The solution was then evaporated and the resulting oil was dissolved in water (100 ml) and washed with isopropyl ether (2×30 ml). Pure compound (VII) (0.65 mmol) was obtained after a RP-HPLC purification step with YMC-Triart Phenyl preparative column (250×50 mm) wherein a linear gradient was used from 0 to 95% acetonitrile in ammonium acetate buffer.

Compound 3 as freeze-dried powder (0.65 mmol) was dissolved in 100 ml of sodium borate buffer (pH 9) and pure compound (VI) (0.65 mmol, see scheme 1) was added to the solution. The mixture was allowed to stir in the dark at room temperature overnight. The reaction was quenched by adding 5% acetic acid solution until pH 7. The crude dark blue reaction mixture was purified on RP-HPLC YMC-Triart Phenyl preparative column (250×50 mm) by eluting with a linear gradient from 0 to 95% acetonitrile in ammonium acetate buffer.

After purification, pure DA364 compound was obtained as a blue freeze-dried powder in 24% yield (0.33 mmol) with respect to azide compound (II).

The invention claimed is:
1. A process for the preparation of a cRGD-Cy5.5 conjugate of formula (I)

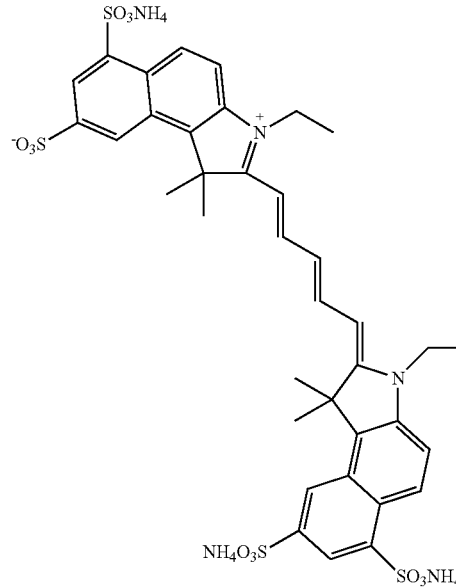
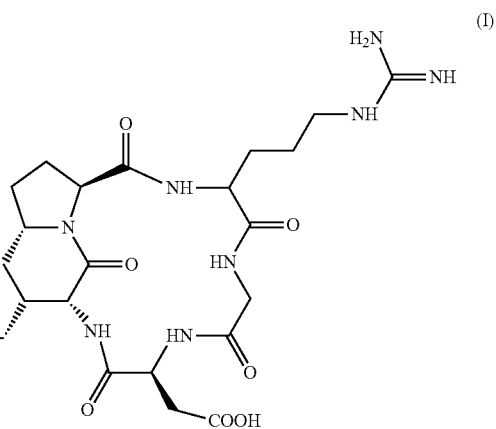
which comprises the steps of:
a) hydrogenating a compound of formula (II)
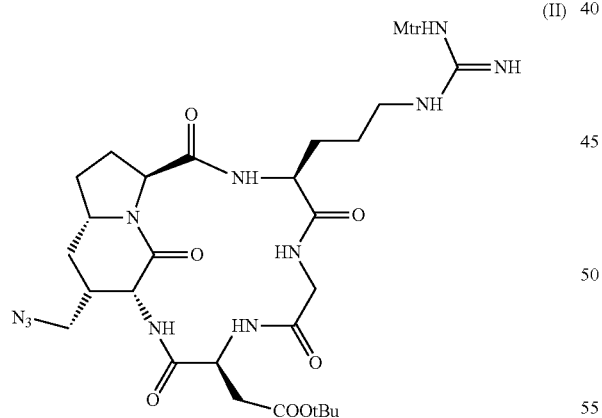
wherein Mtr is a 2,3,6-trimethyl-4-methoxybenzenesulfonyl group, to provide its amino-derivative of formula (III)
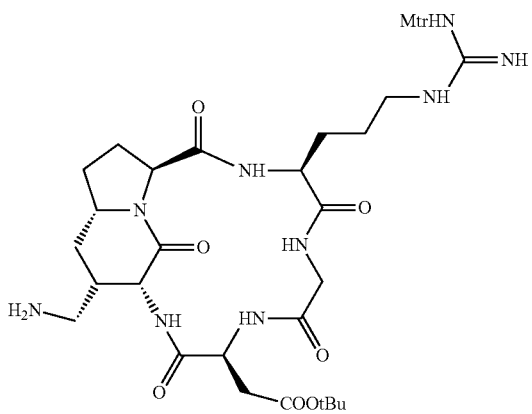
wherein Mtr is as defined above;
b) reacting, in the presence of a base and a coupling reagent, the compound of formula (III) with a compound of formula (IV)

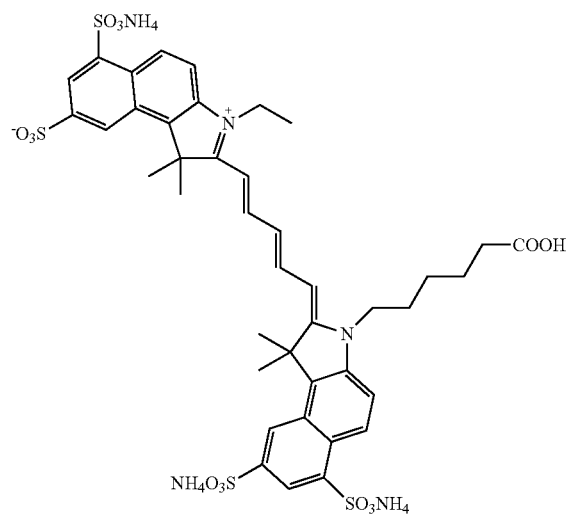

to provide a compound of formula (V)

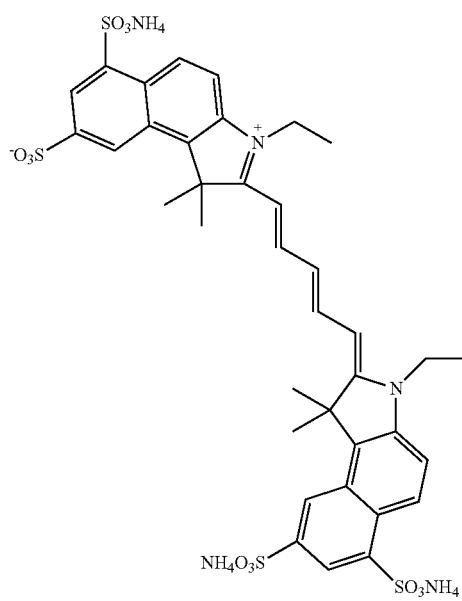

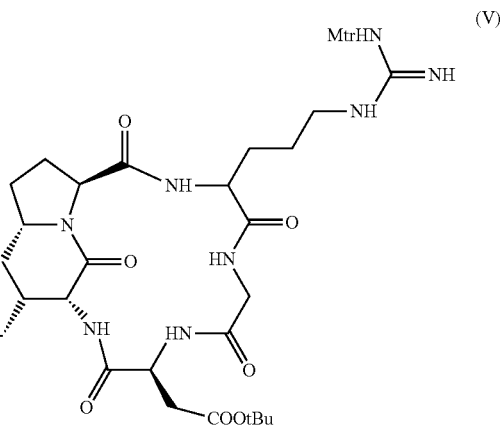

wherein Mtr is as defined above;
c) deprotecting the compound of formula (V) to obtain the compound of formula (I).

2. The process according to claim 1 wherein the compound of formula (II) is dissolved in a solvent, which solvent is an alcohol or a mixture of alcohols.

3. The process according to claim 1 wherein the compound of formula (II) is in a concentration of from 3 to 7 millimolar.

4. The process according to claim 1 wherein the step a) is performed by flowing the compound of formula (II) dissolved in a solvent through a metal catalyst under hydrogen atmosphere.

5. The process according to claim 1 wherein the step a) is carried out at a temperature of from 18° C. to 40° C.

6. The process according to claim 1 wherein the step b) is effected in the presence of a solvent selected from N,N-dimethylformamide, N,N-dimethylacetamide, dimethyl sulfoxide, N-methylpyrrolidinone and acetonitrile.

7. The process according to claim 1 wherein the coupling reagent is selected from the group consisting of N,N,N',N'-tetramethyl-O-(benzotriazol-1-yl)uronium tetrafluoroborate (TBTU), 4-(4,6-dimethoxy-1,3,5-triazin-2-yl)-4-methylmorpholinium chloride (DMTMM), (benzotriazol-1-yloxy)tris(dimethylamino)phosphonium hexafluorophosphate (BOP), (benzotriazol-1-yloxy)tripyrrolidinophosphonium hexafluorophosphate (PyBOP) N,N,N',N'-tetramethyl-O-(7-azabenzotriazol-1-yl)uronium hexafluorophosphate (HATU), N,N,N',N'-tetramethyl-O-(1H-benzotriazol-1-yl)uronium hexafluorophosphate (HBTU) and propylphosphonic anhydride (T3P).

8. The process according to claim 1 wherein the base is selected from the group consisting of N,N-diisopropylethylamine (DIPEA), triethylamine (TEA), tributylamine, N-methylpiperidine and N-methylmorpholine.

9. The process according to claim 1 wherein the compound of formula (IV) is in a concentration of from 5 to 10 mM.

10. The process according to claim 1 wherein the ratio between the compound of formula (IV) and the base is from 1:3 to 1:6 (mol/mol).

11. The process according to claim 1 wherein the step b) is carried out at a temperature of from 20° C. to 25° C.

12. The process according to claim 1 wherein the compound of formula (V) is treated with an acid scavenger cocktail selected from the group consisting of trifluoroacetic acid/phenol/thioanisole/1,2-ethanedithiol/water, trifluoroacetic acid/thioanisole/1,2-ethanedithiol/anisole and trifluoroacetic acid/phenol/water/triisopropylsilane.

13. The process according to claim 12 wherein the ratio between trifluoroacetic acid, thioanisole, 1,2-ethanedithiol and anisole is from 70:15:10:5 to 90:5:3:2.

14. The process according to claim 1 which comprises an additional step d) of purification.

15. The process according to claim 1, wherein the compound of formula (I) is purified by an anion exchange chromatography performed with an agarose matrix resin.

* * * * *